US00PP35593P2

(12) United States Plant Patent
Winslow

(10) Patent No.: US PP35,593 P2
(45) Date of Patent: Jan. 16, 2024

(54) ***PORTULACA* PLANT NAMED 'WNPORMYEL23'**

(50) Latin Name: ***Portulaca oleracea* X *Portulaca umbracticola***
Varietal Denomination: WNPORMYEL23

(71) Applicant: Benjamin K. Winslow, Austin, TX (US)

(72) Inventor: Benjamin K. Winslow, Austin, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/135,161

(22) Filed: Apr. 16, 2023

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Portulaca* plant named 'WNPORMYEL23', characterized by its outwardly spreading to mounding and decumbent plant habit; vigorous growth habit and rapid growth rate; freely branching habit; dense and bushy appearance; early and freely flowering habit; long flowering period; large golden yellow-colored flowers that remain open for an extended period of time during the daytime; and excellent container and garden performance.

2 Drawing Sheets

Figure 1:
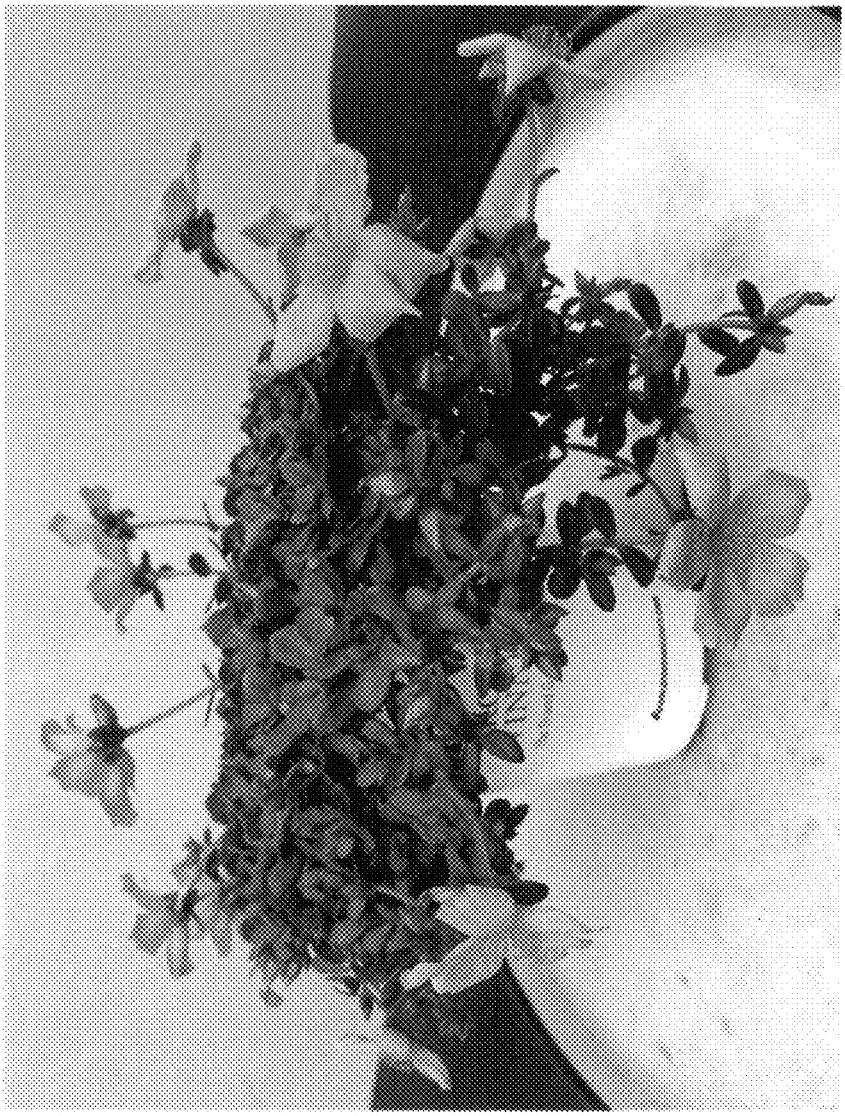

Botanical designation: *Portulaca oleracea* X *Portulaca umbracticola.*
Cultivar denomination: 'WNPORMYEL23'.

BACKGROUND OF THE INVENTION

The present invention relates to a new and distinct cultivar of *Portulaca* plant, botanically known as *Portulaca oleracea* X *Portulaca umbracticola* and hereinafter referred to by the name 'WNPORMYEL23'.

The new *Portulaca* plant is a product of a planned breeding program conducted by the Inventor in Alajuela, Costa Rica and Jacksonville, Texas. The objective of the breeding program is to create new vigorous *Portulaca* plants with numerous attractive flowers that remain open for an extended period of time.

The new *Portulaca* plant originated from a cross-pollination made by the Inventor in Alajuela, Costa Rica on Jun. 1, 2017 of *Portulaca oleracea* 'SAKPOR012', disclosed in U.S. Plant Pat. No. 28,579, as the female, or seed, parent with *Portulaca umbracticola* 'Mojave Yellow', not patented, as the male, or pollen, parent. The new *Portulaca* plant was discovered and selected by the Inventor as a flowering plant from within the progeny of the stated cross-pollination in a controlled greenhouse environment in Jacksonville, Texas on Oct. 12, 2018.

Asexual reproduction of the new *Portulaca* plant by vegetative terminal cuttings in a controlled greenhouse environment in Jacksonville, Texas since Oct. 15, 2018, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPORMYEL23'. These characteristics in combination distinguish 'WNPORMYEL23' as a new and distinct *Portulaca* plant:

1. Outwardly spreading to mounding and decumbent plant habit.
2. Vigorous growth habit and rapid growth rate.
3. Freely branching habit; dense and bushy appearance.
4. Early and freely flowering habit.
5. Long flowering period.
6. Large golden yellow-colored flowers that remain open for an extended period of time during the daytime.
7. Excellent container and garden performance.

Plants of the new *Portulaca* can be compared to plants of the female parent, 'SAKPOR012'. Plants of the new *Portulaca* differ primarily from plants of 'SAKPOR012'in the following characteristics:

1. Plants of the new *Portulaca* are more vigorous than and not as compact as plants of 'SAKPOR012'.
2. Plants of the new *Portulaca* have larger flowers than plants of 'SAKPOR012'.
3. Flowers of plants of the new *Portulaca* are darker yellow in color than flowers of plants of 'SAKPOR012'.

Plants of the new *Portulaca* can be compared to plants of the male parent, 'Mojave Yellow'. Plants of the new *Portulaca* differ primarily from plants of 'Mojave Yellow' in the following characteristics:

1. Plants of the new *Portulaca* are more upright than and not as prostrate as plants of 'Mojave Yellow'.
2. Plants of the new *Portulaca* are more vigorous than plants of 'Mojave Yellow'.
3. Plants of the new *Portulaca* have larger flowers than plants of 'Mojave Yellow'.
4. Flowers of plants of the new *Portulaca* are darker yellow in color than flowers of plants of 'Mojave Yellow'.
5. Flowers of plants of the new *Portulaca* stay open longer during the daytime than flowers of plants of 'Mojave Yellow'.

Plants of the new *Portulaca* can be compared to plants of the *Portulaca oleracea* 'POR16000', disclosed in U.S. Plant Pat. No. 32,693. In side-by-side comparisons, plants of the new *Portulaca* differ primarily from plants of 'POR16000' in the following characteristics:

1. Plants of the new *Portulaca* are more upright than and not as prostrate as plants of 'POR16000'.
2. Plants of the new *Portulaca* are more vigorous than plants of 'POR16000'.
3. Plants of the new *Portulaca* have more flowers on the crown of the plant than plants of 'POR16000'.
4. Flowers of plants of the new *Portulaca* are yellow in color whereas flowers of plants of 'POR16000' are dark red in color.
5. Flowers of plants of the new *Portulaca* stay open longer during the daytime than flowers of plants of 'POR16000'.

Plants of the new *Portulaca* can also be compared to plants of the *Portulaca oleracea* 'SAKPOR011', disclosed in U.S. Plant Pat. No. 28,526. In side-by-side comparisons, plants of the new *Portulaca* differ primarily from plants of 'SAKPOR011' in the following characteristics:

1. Plants of the new *Portulaca* are more upright and open than and not as prostrate and dense as plants of 'SAKPOR011'.
2. Plants of the new *Portulaca* are more vigorous than plants of 'SAKPOR011'.
3. Flowers of plants of the new *Portulaca* are yellow in color whereas flowers of plants of 'SAKPOR011' are pink in color with yellow-colored centers.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

The photograph on the first sheet (FIG. 1) is a side perspective view of a typical flowering plant of 'WNPORMYEL23' grown in a container.

Figure 2:
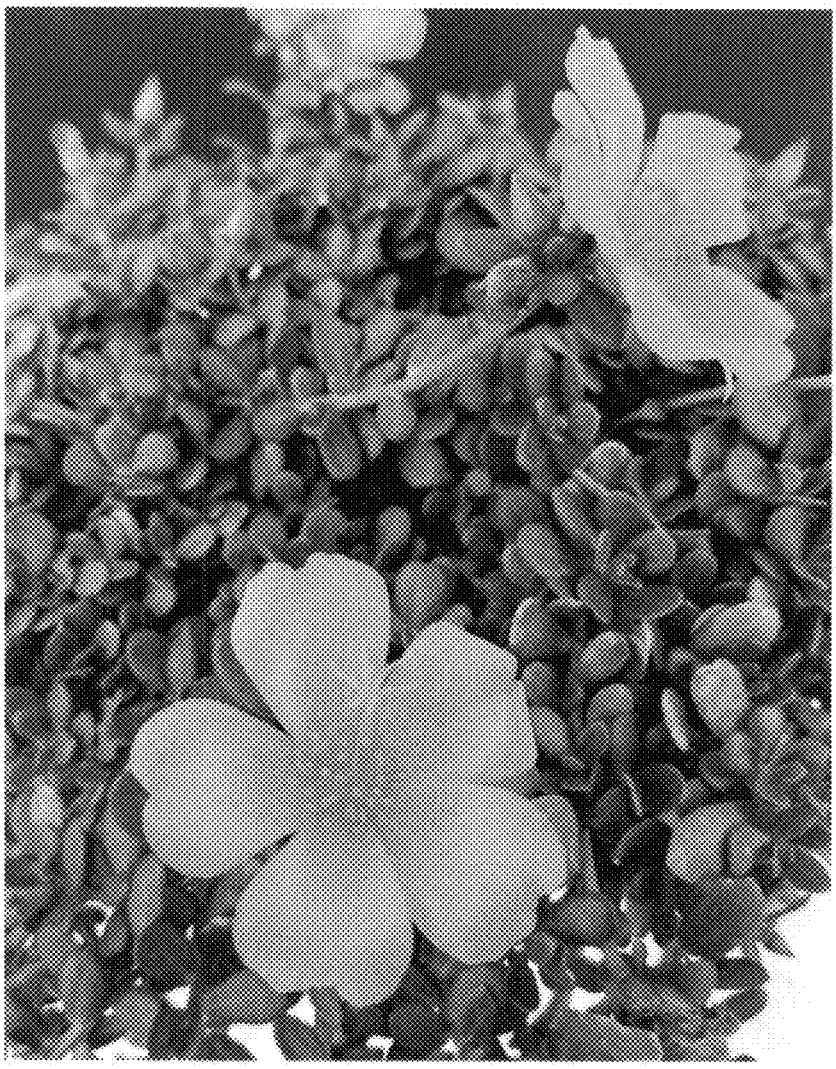

The photograph on the second sheet (FIG. 2) is a close-up view of a typical flowering plant of 'WNPORMYEL23'.

DETAILED BOTANICAL DESCRIPTION

The aforementioned photographs and following observations and measurements describe plants grown during the summer in 740-ml containers in an acrylic-covered greenhouse in Carlton, Michigan and under cultural practices typical of commercial *Portulaca* production. During the production of the plants, day temperatures ranged from 18 C to 32 C and night temperatures ranged from 18 C to 24 C. Plants were pinched one time seven weeks after planting rooted young plants; and plants were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Portulaca oleracea* X *Portulaca umbracticola* 'WNPORMYEL23'.

Parentage:

*Female, or seed, parent.*—*Portulaca oleracea* 'SAKPOR012', disclosed in U.S. Plant Pat. No. 28,579.

*Male or pollen parent.*—*Portulaca umbracticola* 'Mojave Yellow', not patented.

Propagation:

*Type*.—By vegetative terminal cuttings.

*Time to initiate roots, summer*.—About three to four days at ambient temperatures about 28 C.

*Time to initiate roots, winter*.—About five to seven days at ambient temperatures about 20 C.

*Time to produce a rooted young plant, summer*.—About three to four weeks at ambient temperatures about 28 C.

*Time to produce a rooted young plant, winter*.—About four to five weeks at ambient temperatures about 20 C.

*Root description*.—Fine, fleshy; typically white in color, actual color of the roots is dependent on substrate composition, water quality, fertilizers, substrate temperature and age of roots.

*Rooting habit*.—Freely branching; medium density.

Plant description:

*Plant and growth habit*.—Outwardly spreading to mounding and decumbent plant habit; vigorous growth habit and rapid growth rate.

*Branching habit*.—Freely branching habit about six to ten primary lateral branches per plant each with secondary lateral branches developing potentially at every node; pinching enhances branching potential.

*Plant height*.—About 5 cm.

*Plant diameter* (*area of spread*).—About 42 cm by 43 cm.

Lateral branch/peduncle description:

*Length*.—About 26 cm.

*Diameter*.—About 4 mm.

*Internode length*.—Variable, about 1.5 cm.

*Strength*.—Moderately strong; very flexible.

*Texture and luster*.—Smooth, glabrous; moderately glossy.

*Color, developing*.—Close to 144A.

*Color, developed*.—Close to 144A, variably overlain with close to 58A.

Leaf description:

*Arrangement*.—Opposite, simple.

*Length*.—About 2.4 cm.

*Width*.—About 1.2 cm.

*Shape*.—Obovate.

*Apex*.—Rounded, obtuse.

*Base*.—Cuneate.

*Margin*.—Entire.

*Texture and luster, upper and lower surfaces*.—Smooth, glabrous; fleshy, succulent; moderately glossy; irridescent.

*Venation pattern*.—Pinnate.

*Color*.—Developing leaves, upper surface: Close to 146A to slightly darker green than 146A. Developing leaves, lower surface: Close to 146B to slightly darker green than 146B. Fully expanded leaves, upper surface: Darker green than 146A; venation, close to 146A. Fully expanded leaves, lower surface: Slightly darker green than 146B; venation, slightly darker green than 146B.

*Petioles*.—Length: About 2 mm. Diameter: About 1.5 mm. Texture and luster, upper and lower surfaces: Smooth, glabrous; semi-glossy. Strength: Moderately strong. Color, upper and lower surfaces: Close to 144A.

Flower description:

*Flower arrangement*.—Single rotate and cupped flowers; freely flowering habit with three to five flowers per terminal; numerous flowers developing per plant during the flowering season; flowers face mostly upright to slightly outwardly.

*Fragrance*.—None detected.

*Natural flowering season*.—Plants begin flowering about seven weeks after planting; in the garden, plants flower continuously from spring until autumn in Michigan.

*Flower longevity*.—Flowers last about one day on the plant; flowers not persistent.

*Flower buds*.—Length: About 8.5 mm. Diameter: About 4 mm. Shape: Ovoid. Texture and luster: Smooth, glabrous; somewhat glossy. Color, developing sepals: Close to 144A.

*Flower diameter*.—About 3.6 cm.

*Flower length* (*height*).—About 1 cm.

*Petals*.—Quantity per flower: Corolla consists of five petals fused at the base. Length: About 1.7 cm. Width: About 1.3 cm. Shape: Obcordate. Apex: Emarginate. Base: Fused, truncate. Margin: Entire, slightly undulate. Texture and luster, upper surface: Smooth, glabrous, satiny; glossy. Texture and luster, lower surface: Smooth, glabrous; moderately glossy. Color: When opening and fully opened, upper surface: Close to 13A, iridescent; venation, close to 13A; color does not change with subsequent development. When opening and fully opened, lower surface: Close to 11A; venation, close to 11A; color does not change with subsequent development.

*Sepals*.—Quantity per flower: Two fused into a tubular calyx. Length: About 8 mm. Width: About 4 mm. Shape: Broadly ovate. Apex: Acute. Margin: Entire. Texture and luster, upper and lower surfaces: Smooth, glabrous; somewhat glossy. Color, upper surface: Close to 154C, translucent. Color, lower surface: Close to 144A, translucent.

*Reproductive organs*.—Androecium: Quantity of stamens per flower: About 56. Filament length: About 4 mm. Filament color: Close to 9A. Anther shape: Oblong. Anther length: Less than 1 mm. Anther color: Close to 17A. Amount of pollen: Abundant. Pollen color: Close to 17A. Gynoecium: Pistil length: About 7 mm. Style length: About 5 mm. Style color: Close to 9A. Stigma diameter: About 4.5 mm. Stigma color: Close to 9A. Ovary color: Close to 154D. Fruits and seeds: To date, fruit and seed development have not been observed on plants of the new *Portulaca*.

Garden performance: Plants of the new *Portulaca* have been observed to have excellent garden performance and to tolerate temperatures ranging from about 2 C to about 35 C.

Pathogen & pest resistance: To date, plants of the new *Portulaca* have not been shown to be resistant to pathogens and pests common to *Portulaca* plants.

It is claimed:

1. A new and distinct *Portulaca* plant named 'WNPORMYEL23' as illustrated and described.

* * * * *